United States Patent

Hoffmann

[11] 4,317,783
[45] Mar. 2, 1982

[54] 1-OXO-3-METHYL-2-BUTENE PHOSPHONIC ACID ESTERS

[75] Inventor: Hellmut Hoffmann, Wuppertal, Fed. Rep. of Germany

[73] Assignee: Bayer Aktiengesellschaft, Leverkusen, Fed. Rep. of Germany

[21] Appl. No.: 170,377

[22] Filed: Jul. 21, 1980

[30] Foreign Application Priority Data

Aug. 9, 1979 [DE] Fed. Rep. of Germany ....... 2932262

[51] Int. Cl.³ .......................... C07F 9/40; C07C 57/66
[52] U.S. Cl. ..................................... 260/937; 260/946; 260/544 Y; 260/969; 260/968; 260/941
[58] Field of Search ............................... 260/946, 937

[56] References Cited

U.S. PATENT DOCUMENTS

2,491,920 12/1949 Ernsberger .......................... 260/946
2,748,153 5/1956 Cope et al. ........................... 260/946
3,483,279 12/1969 Davis et al. .......................... 260/937

*Primary Examiner*—Anton H. Sutto
*Attorney, Agent, or Firm*—Sprung, Felfe, Horn, Lynch & Kramer

[57] ABSTRACT

A process for the preparation of an α-oxo-α-(3-alkoxycarbonyl-2,2-dimethyl-cycloprop-1-yl)-methane-phosphonic acid ester of the formula

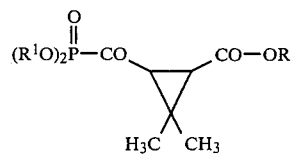

in which
R is alkyl or a radical customary in the alcohol component of pyrethroids, and R¹ is alkyl or phenyl, or the two radicals R¹ together are alkanediyl, comprising reacting Δ,Δ-dimethyl-acrylic acid chloride of the formula

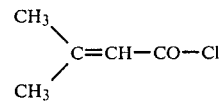

with a phosphorous acid ester of the formula

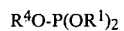

in which
R⁴ is alkyl, at a temperature between about 0° and 100° C., to produce the novel compound 1-oxo-3-methyl-2-butene-phosphonic acid of the formula

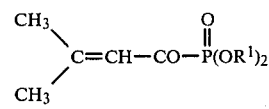

which is then reacted with a sulphuranylidene-acetic acid ester of the formula

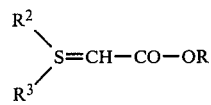

in which
R² and R³ each independently is alkyl or together are alkanediyl, at a temperature between about 0° and 100° C.

1 Claim, No Drawings

1-OXO-3-METHYL-2-BUTENE PHOSPHONIC ACID ESTERS

The invention relates to an unobvious process for the preparation of certain α-oxo-α-(3-alkoxycarbonyl-2,2-dimethylcycloprop-1-yl)-methane-phosphonic acid esters (which can be used as intermediate products for the preparation of pesticides) and to new intermediate products for this process and to a process for their preparation.

α-Oxo-α-(3-alkoxycarbonyl-2,2-dimethyl-cycloprop-1-yl)-methane-phosphonic acid esters are the subject of German Patent Applications P 29 17 260.3 [=Le A 19 632] and P 29 29 670.6 [=Le A 19 821].

The present invention now provides:

(1) a process for the preparation of an α-oxo-α-(3-alkoxycarbonyl-2,2-dimethyl-cycloprop-1-yl)-methane-phosphonic acid ester of the general formula

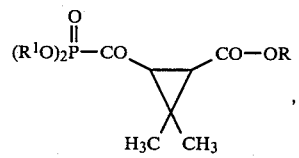

in which
R represents alkyl or a radical customary in the alcohol component of pyrethroids and
$R^1$ represents alkyl or phenyl, or
the two radicals $R^1$ together represent straightchain or branched alkanediyl (alkylene),
characterized in that a 1-oxo-3-methyl-2-butene-phosphonic acid ester of the general formula

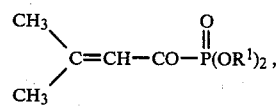

in which
$R^1$ has the meaning indicated above, is reacted with a sulphuranylidene-acetic acid ester of the general formula

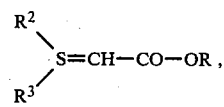

in which
R has the meaning indicated above and
$R^2$ and $R^3$ individually represent alkyl or together represent alkanediyl (alkylene),
if appropriate in the presence of a diluent, at a temperature between about 0° and 100° C.;

(2), as new compounds, the 1-oxo-3-methyl-2-butene-phosphonic acid esters of the general formula

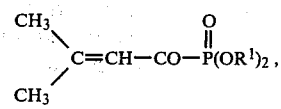

in which
$R^1$ represents alkyl or phenyl, or
the two radicals $R^1$ together represent straightchain or branched alkanediyl (alkylene);
and (3) a process for the preparation of a 1-oxo-3-methyl-2-butene-phosphonic acid ester of the formula (II) above, characterized in that β,β-dimethyl-acrylic acid chloride, of the formula

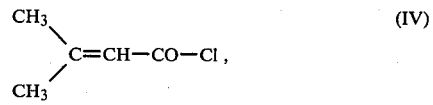

is reacted with a phosphorous acid ester of the general formula

in which
$R^1$ has the meaning indicated above and
$R^4$ represents alkyl, preferably methyl or ethyl, if appropriate in the presence of a diluent, at a temperature between about 0° and 100° C.

It is surprising that α-oxo-α-(3-alkoxy-carbonyl-2,2-dimethyl-cycloprop-1-yl)-methane-phosphonic acid esters are obtained in very high yields by the process according to the invention since, in reactions of β,β-dimethylacrylic acid derivatives with sulpuranylidene-acetic acid esters, the corresponding cyclopropane derivatives are in general formed only in low yields.

If, for example, 1-oxo-3-methyl-2-butene-phosphonic acid dimethyl ester and dimethylsulphuranylidene-acetic acid methyl ester are used as starting materials, the reaction, according to the invention, of these compounds can be outlined by the following equation:

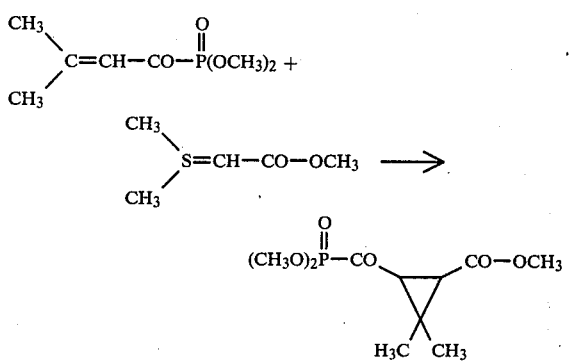

The process according to the invention described above under (1) ("process (1)") is preferably carried out using a suitable solvent or diluent. Possible solvents and diluents are virtually any of the inert organic solvents. These include, as preferences, aliphatic and aromatic, optionally chlorinated hydrocarbons, for example pentane, hexane, heptane, cyclohexane, benzene, toluene, xylenes, methylene chloride, ethylene chloride, chloroform, carbon tetrachloride, chlorobenzene and dichlorobenzenes; ethers, for example diethyl ether, dibutyl ether, tetrahydrofuran and dioxane; and nitriles, for example acetonitrile and propionitrile.

The reaction temperature in process (1) is in general kept between 0° and 100° C., preferably between about 20° and 80° C. The process is in general carried out under normal pressure.

The starting compounds of the formulae (II) and (III) are usually employed in approximately equimolar amounts for carrying out process (1), that is to say the molar ratio of the components is 1 to 1±0.1. In a preferred embodiment of the process, the 1-oxo-3-methyl-2-butene-phosphonic acid ester is initially introduced, if appropriate in one of the diluents indicated above, and the sulphuranylidene-acetic acid ester is added. The mixture of the components is stirred at the temperature indicated above until the reaction has ended; the solvent is then carefully distilled off in vacuo, whereupon the product of the formula (I) remains as an oily residue.

Formula (II) provides a definition of the new 1-oxo-3-methyl-2-butene-phosphonic acid esters to be used as starting substances. Preferably, in this formula, $R^1$ represents $C_1$–$C_4$-alkyl or phenyl, or the two radicals $R^1$ together represent 2,2-dimethylpropane-1,3-diyl.

Examples which may be mentioned are 1-oxo-3-methyl-2-butene-phosphonic acid dimethyl ester, diethyl ester and diphenyl ester and 2-oxo-2(1-oxo-3-methyl-2-buten-1-yl)-5,5-dimethyl-1,3,2-dioxaphosphorinane.

The new 1-oxo-3-methyl-2-butene-phosphonic acid esters of the formula (II) are obtained by the process described above under (3), by reacting β,β-dimethylacrylic acid chloride of the formula (IV) above with phosphorous acid esters of the formula (V) above, for example with trimethyl phosphite or triethyl phosphite or 2-methoxy- or 2-ethoxy-5,5-dimethyl-1,3,2-dioxaphosphorinane, if appropriate in the presence of a diluent, for example methylene chloride (or another of the solvents indicated above for process (1)), at a temperature between 0° and 100° C., preferably between about 20° and 80° C., and if appropriate distilling the crude product.

The phosphorous acid esters to be employed as starting materials are known, as is β,β-dimethyl-acrylic acid chloride.

Formula (III) provides a definition of the sulphuranylidene-acetic acid esters to be used as further starting materials in process (1).

Preferably, in this formula,

R represents $C_1$–$C_4$-alkyl and $R^2$ and $R^3$ individually represent methyl or together represent butane-1,4-diyl (tetramethylene).

Examples of the starting materials of the formula (III) which may be mentioned are: dimethylsulphuranylidene-acetic acid methyl ester, ethyl ester, n-propyl ester, iso-propyl ester, n-butyl ester, iso-butyl ester, sec.-butyl ester and tert.-butyl ester and tetramethylenesulphuranylidene-acetic acid methyl ester, ethyl ester, n-propyl ester, iso-propyl ester, n-butyl ester, iso-butyl ester, sec.-butyl ester and tert.-butyl ester.

Compounds of the formula (III) are known (see J.Org.Chem. 32 (1967), 3351; U.S. Pat. No. 3,644,487 and DE-OS (German Published Specification) 2,724,734).

3-Formyl-2,2-dimethyl-cyclopropane-1-carboxylic acid esters are obtained from the α-oxo-α-(3-alkoxycarbonyl-2,2-dimethyl-cycloprop-1-yl)-methanephosphonic acid esters of the formula (I) by reaction with reducing agents, for example sodium tetrahydridoborate (sodium boranate), if appropriate using diluents, for example water and/or methanol and/or methylene chloride, at temperatures between −20° and +50° C., preferably between −10° and +30° C., and reaction of the resulting α-hydroxy-α-(3-alkoxycarbonyl-2,2-dimethylcycloprop-1-yl)-methane-phosphonic acid esters with aqueous alkali metal hydroxide solutions, for example aqueous sodium hydroxide solution, if appropriate in the presence of a water-immiscible solvent, for example methylene chloride, at temperatures between 0° and 100° C., preferably between 0° and 50° C., in accordance with the equation below (see Chem. Ber. 103 (1970), 2984–2986):

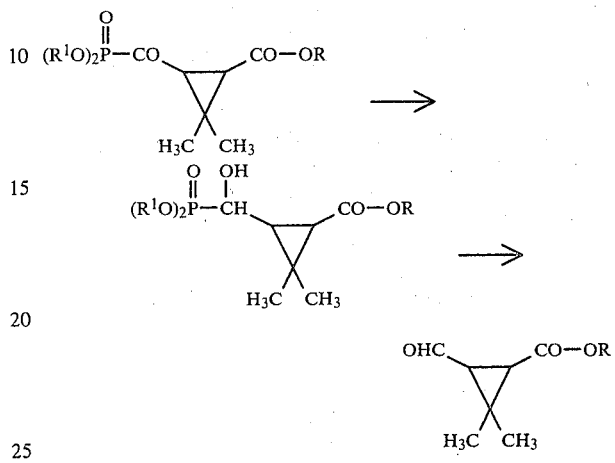

3-Formyl-2,2-dimethyl-cyclopropane-1-carboxylic acid esters can be used as intermediate products for the preparation of insecticidally and acaricidally active pyrethroids (see DE-OS (German Published Specification) 2,326,077).

EXAMPLE

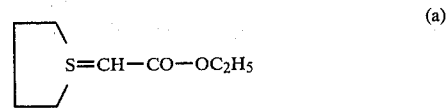

(a)

A solution of 12 g of potassium hydroxide in 12 ml of water mixed with 55 ml of saturated potassium carbonate solution was added to an intensively stirred solution, cooled to 10° to 15° C., of 52 g (0.2 mol) of tetramethylenesulphonium-acetic acid ethyl ester bromide in 180 ml of chloroform. The reaction mixture was stirred at 10° C. for 15 minutes and then filtered. The two phases of the filtrate were separated. The chloroform phase was dried over sodium sulphate and, after filtration, the solvent was carefully distilled off from the filtrate under reduced pressure, during which the bath temperature did not exceed 30° C. The product which remained was employed as tetramethylenesulphuranylidene-acetic acid ethyl ester (100% pure).

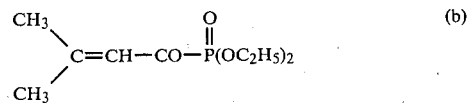

(b)

83 g (0.5 mol) of triethyl phosphite were added dropwise to a solution of 60 g (0.5 mol) of β,β-dimethylacrylic acid chloride in 200 ml of methylene chloride in the course of one hour. The reaction mixture was stirred for a further hour at 40° to 45° C.; the solvent was then distilled off under reduced pressure and the crude product which remained was purified by vacuum distillation. 90 g (82% of theory) of 1-oxo-3-methyl-2-butylene-phosphonic acid diethyl ester of boiling point 72° C./0.01 mbar were obtained.

Elementary analysis: calculated: C 49.1%; H 7.7%; O 29.1%; P 14.1%; found: C 48.5%; H 7.6%; O 28.9%; P 13.4%.

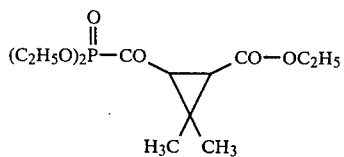
(c)

36 g (0.2 mol) of tetramethylenesulphuranylidene-acetic acid ethyl ester were added to a solution of 44 g (0.2 mol) of 1-oxo-3-methyl-2-butene-phosphonic acid diethyl ester in 150 ml of toluene in the course of 10 minutes. During this addition, the internal temperature rose to about 55° C. The reaction mixture was stirred for some hours; the solvent was then carefully distilled off under reduced pressure. 58 g (95% of theory) of α-oxo-α-(3-ethoxycarbonyl-2,2-dimethyl-cycloprop-1-yl)-methane-phosphonic acid diethyl ester were obtained as an oily residue.

Elementary analysis: calculated: C 51.0%; H 7.5%; O 31.4%; P 10.1% found: C 50.4%; H 7.4%; O 31.3%; P 9.7%.

It will be appreciated that the instant specification and examples are set forth by way of illustration and not limitation, and that various modifications and changes may be made without departing from the spirit and scope of the present invention.

I claim:

1. A 1-oxo-3-methyl-2-butene-phosphonic acid ester of the formula

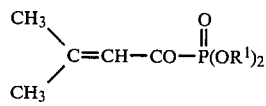

in which
R$^1$ is C$_{1-4}$-alkyl or phenyl, or
the two radicals R$^1$ together are 2,2-dimethyl-propane-1,3-diyl.

* * * * *